(12) United States Patent
Chiba et al.

(10) Patent No.: US 11,661,575 B2
(45) Date of Patent: May 30, 2023

(54) CELL CULTURE DEVICE

(71) Applicant: FULLSTEM CO., LTD., Naha (JP)

(72) Inventors: Shunmei Chiba, Naha (JP); Young-Jin Lee, Seoul (KR); Takaki Ushifusa, Fukuoka (JP)

(73) Assignee: FULLSTEM CO., LTD., Naha (JP)

( * ) Notice: Subject to any disclaimer, the term of this patent is extended or adjusted under 35 U.S.C. 154(b) by 161 days.

(21) Appl. No.: 16/632,765

(22) PCT Filed: Feb. 14, 2019

(86) PCT No.: PCT/JP2019/005203
§ 371 (c)(1),
(2) Date: Jan. 21, 2020

(87) PCT Pub. No.: WO2019/160000
PCT Pub. Date: Aug. 22, 2019

(65) Prior Publication Data
US 2021/0155887 A1  May 27, 2021

(30) Foreign Application Priority Data

Feb. 15, 2018  (JP) .............................. JP2018-024689

(51) Int. Cl.
*C12M 1/12* (2006.01)
*C12M 3/06* (2006.01)
(Continued)

(52) U.S. Cl.
CPC ............ *C12M 25/14* (2013.01); *C12M 27/16* (2013.01); *C12M 27/22* (2013.01); *C12N 5/0663* (2013.01); *C12N 5/0667* (2013.01); *C12N 5/0668* (2013.01)

(58) Field of Classification Search
CPC ...... C12M 25/14; C12M 27/16; C12M 27/22; C12N 5/0663; C12N 5/0667; C12N 5/0668
See application file for complete search history.

(56) References Cited

U.S. PATENT DOCUMENTS

| | | | |
|---|---|---|---|
| 7,033,823 | B2 | 4/2006 | Chang |
| 2003/0143727 | A1 | 7/2003 | Chang |

(Continued)

FOREIGN PATENT DOCUMENTS

| | | |
|---|---|---|
| CN | 105579576 A | 5/2016 |
| JP | H02-57174 A | 2/1990 |

(Continued)

OTHER PUBLICATIONS

International Searching Authority, International Search Report and Written Opinion for International Application No. PCT/JP2019/005203, dated Apr. 23, 2019, (9 pages), Tokyo, Japan.

*Primary Examiner* — William H. Beisner
*Assistant Examiner* — Danielle B Henkel
(74) *Attorney, Agent, or Firm* — Alston & Bird LLP

(57) ABSTRACT

Provided is a cell culture device that has a simple structure and ensures sufficient nutrient supply to cells and oxygenation of the cells to thereby enable mass cell culture. The cell culture device comprises: a cell culture container which is an approximately cylindrical body provided with a flat bottom part at the lower end; a dish-shaped body having an approximately disc shape which is provided with a plurality of magnetic attraction members, said magnetic attraction members being positioned in the circumferential part at equal intervals, and horizontally disposed in a non-contact state within a hollow space inside the cell culture container; and a cyclic body which is provided with a plurality of magnetic attraction members and positioned outside the cell culture container so that the cell culture container is located within (Continued)

the cycle thereof. The cyclic body and the dish-shaped body move vertically in magnetic conjunction to thereby agitate a medium and supply nutrients to cells.

11 Claims, 11 Drawing Sheets

(51) Int. Cl.
*C12M 1/00* (2006.01)
*C12N 5/0775* (2010.01)

(56) References Cited

U.S. PATENT DOCUMENTS

| | | |
|---|---|---|
| 2006/0024823 A1 | 2/2006 | Ishikawa et al. |
| 2006/0207944 A1* | 9/2006 | Siddiqi ................. B01F 33/451 |
| | | 210/695 |
| 2007/0231887 A1* | 10/2007 | McGrath ................. C12M 29/04 |
| | | 435/297.5 |
| 2011/0117639 A1 | 5/2011 | Suazo et al. |
| 2013/0189723 A1 | 7/2013 | Felder et al. |
| 2013/0260364 A1 | 10/2013 | Zhang |
| 2016/0228606 A1* | 8/2016 | Danti .................. A61L 27/3645 |
| 2017/0233693 A1* | 8/2017 | Frei ..................... B01F 11/0008 |
| | | 422/307 |

FOREIGN PATENT DOCUMENTS

| | | |
|---|---|---|
| JP | 2003-235539 A | 8/2003 |
| JP | 2004-313008 A | 11/2004 |
| JP | 2006-034200 A | 2/2006 |
| JP | 2007-203244 | 8/2007 |
| JP | 2007-535902 A | 12/2007 |
| JP | 4430317 B2 | 3/2010 |
| WO | WO-00/05942 | 2/2000 |
| WO | WO-2015/040554 A1 | 3/2015 |

* cited by examiner

FIG.5
(A)
(B)
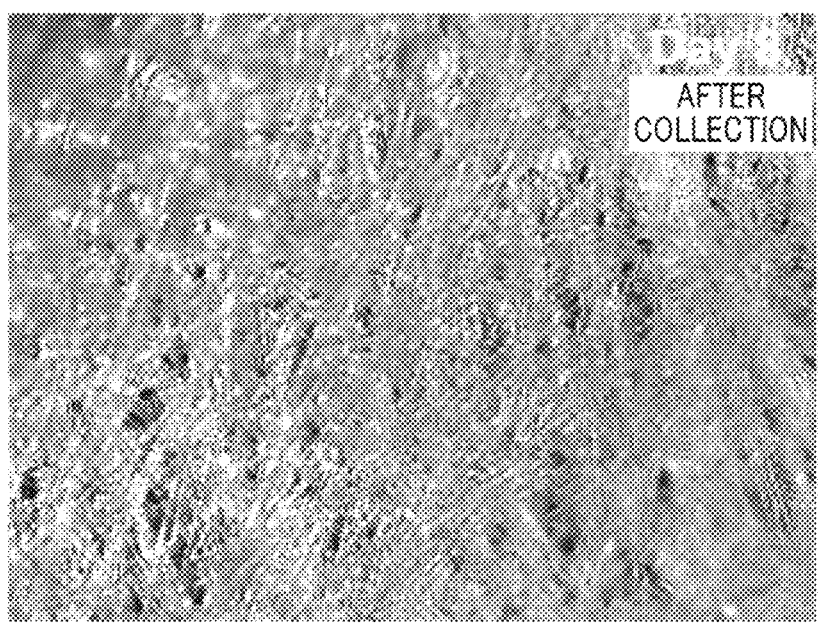

FIG.7
(A) 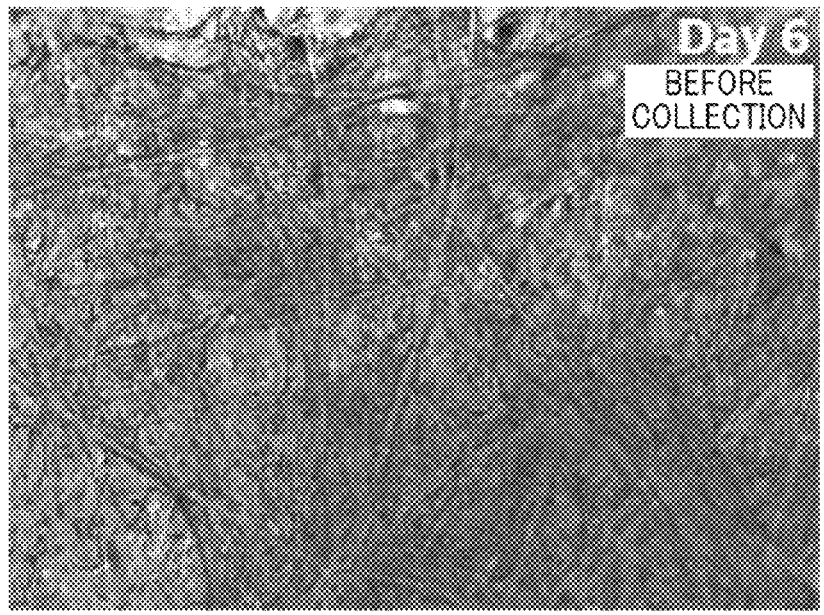
(B) 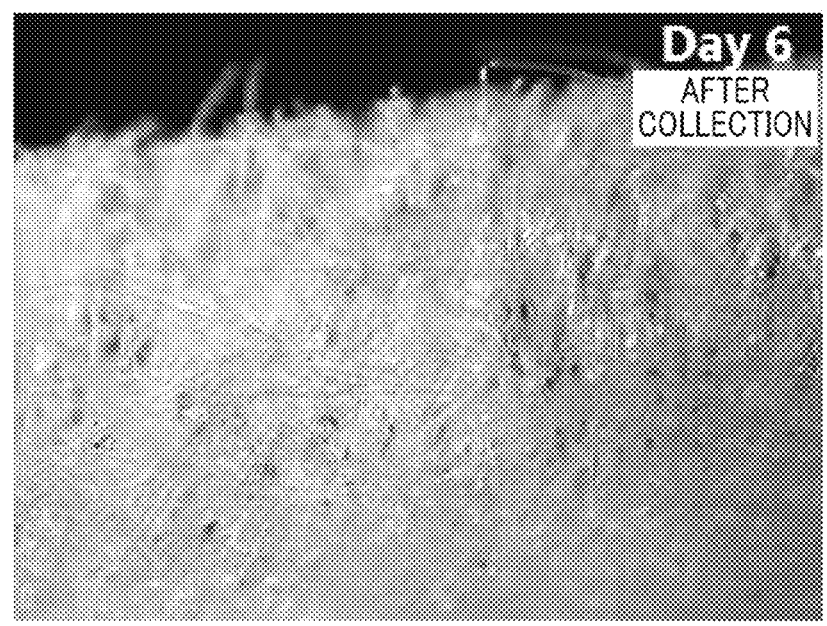

FIG.9
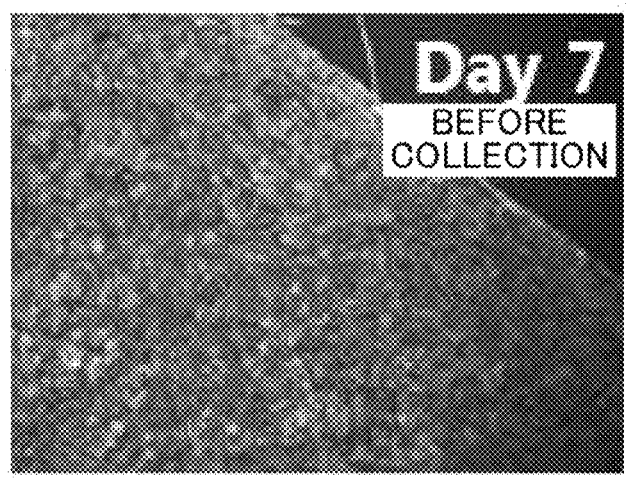

FIG.10
(A)
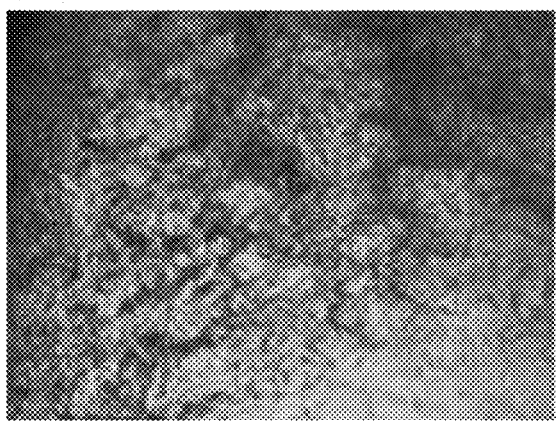
(C)
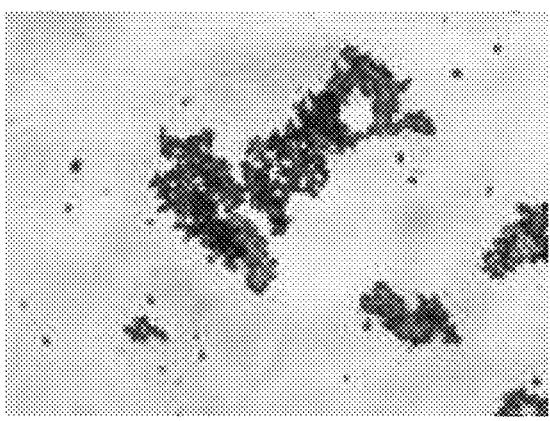
(B)
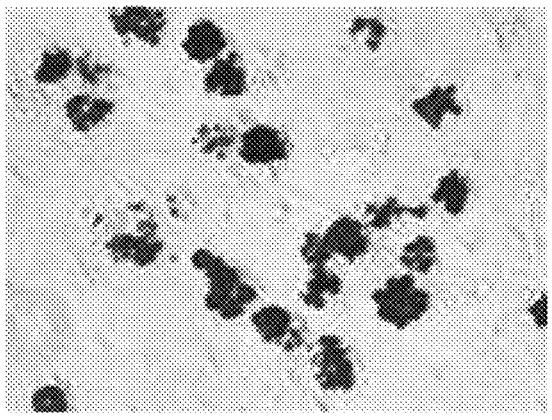

CELL CULTURE DEVICE

CROSS REFERENCE TO RELATED APPLICATIONS

This application is a national stage application, filed under 35 U.S.C. § 371, of International Application No. PCT/JP2019/005203, filed Feb. 14, 2019, which international application claims priority to and the benefit of Japanese Application No. 2018-024689, filed Feb. 15, 2018; the contents of both of which as are hereby incorporated by reference in their entireties.

BACKGROUND

Technical Field

The present invention relates to a cell culture device that allows for medium agitation as well as the supply of nutrients to cells and oxygenation of the cells with simple operations, thereby enabling mass cell culture.

Description of Related Art

Pluripotent stem cells (embryonic stem cells and induced pluripotent stem (iPS) cells) have been acknowledged as important cell sources for regenerative medicine due to their unlimited proliferative capacity and pluripotency. The treatment of cirrhosis, blood diseases, and myocardial infarctions, the construction of blood vessels, the regeneration of bones and cornea, and obtainment of skin for grafting, for example, are considered to be regenerative medicine using stem cells. In regenerative medicine, cells and organs of interest are grown from stem cells or the like in a culture dish and are transplanted to a person. Recently, angiogenesis has been performed from stem cells derived from bone marrow to successfully treat angina pectoris and myocardial infarctions.

In recent years, there has been a demand for a cell culture device that can efficiently mass culture stem cells in an artificial environment for the fields of pharmaceutical production, gene therapy, regenerative medicine, immunotherapy, and so on.

FIG. 11 illustrates a conventional cell culture device. As shown in FIG. 11, the conventional cell culture device includes a first chamber 810, a porous scaffold 820, and a second chamber 830. The second chamber 830 has a bellows-shape that can be compressed and decompressed. In FIG. 11, the second chamber 830 is in an uncompressed shape, which is a state where the second chamber is filled with a culture solution and in which the scaffold 820 is indirectly exposed to a gas environment so that cells undergo oxygenation. In FIG. 12, the second chamber 830 is in a compressed shape, so that the culture solution is pushed upward to move into the first chamber 810. The scaffold 820 is therefore immersed in the culture solution, and the cells are supplied with nutrients. Turning back to FIG. 12, the second chamber 830 is in an uncompressed shape again, so that the culture solution moves downward and fills the second chamber 830.

However, in the cell culture device described above, since the second chamber 830 is bellows-shaped, cells that have moved to the second chamber 830 enter into the projected outer portion of the bellow-shape, and thereafter, such cells are less likely to be affected by the vertical movement of the culture solution caused by the compression and non-compression of the second chamber 830. As a result, oxygenation of the cells may become difficult. In addition, even in a state in which the second chamber 830 has a bellows shape that has been compressed, the culture solution particularly in a central portion of the second chamber 830 cannot be completely returned to the first chamber 810 due to the structure of the bellows shape. In order to seed cells on porous scaffold 820, a cell suspension is placed in the first chamber 810 and left standing still, or the cells are made to adhere while compressing and uncompressing the bellows-shape; however, both of these methods are inefficient because there will be a cell suspension that is unable to adhere due to a dead space and a dead volume that have been created.

Patent Document 1: Japanese Patent No. 4430317.

BRIEF SUMMARY

In view of the foregoing problem, the object of the present invention is to provide a cell culture device having a simple structure and allowing the supply of sufficient nutrients to cells and oxygenation to the cells, thereby enabling mass culture of stem cells.

A cell culture device of the present invention includes: a cell culture vessel which is approximately a cylindrical body having a flat bottom part at a lower end and a hollow space to be filled with a medium for culturing cells; a dish-shaped body which is approximately disc-shaped and which has a diameter slightly smaller than a diameter of the approximately cylindrical body as the cell culture vessel, the dish-shaped body including a plurality of magnetic attraction members made of magnets or ferromagnets arranged at equal intervals at a circumferential portion of the dish-shaped body, the dish-shaped body being arranged horizontally in the hollow space of the cell culture vessel; and an annular body which is approximately ring shaped and configured to move in a vertical direction, the annular body including a plurality of magnetic attraction members made of magnets each corresponding to, and attracting with a magnetic force, associated one of the magnetic attraction members of the dish-shaped body, the annular body being arranged on an outer side of the cell culture vessel so as to position the cell culture vessel within the annular body, the annular body moving upward and causing the dish-shaped body to move upward in conjunction with the upward movement of the annular body due to the magnetic force so that the medium filling the hollow space of the cell culture vessel is pushed up from a bottom, and the annular body moving downward and causing the dish-shaped body to move downward in conjunction with the downward movement of the annular body due to the magnetic force so that the medium filling the hollow space of the cell culture vessel falls with gravity.

The present invention makes it possible to supply sufficient nutrients to cells and oxygenate the cells even with a simple structure, thereby enabling mass culture of stem cells.

BRIEF DESCRIPTION OF THE FIGURES

In FIG. 5, (A) is a photomicrograph showing the adipose-derived mesenchymal stem cells on day 8 of culture before they were collected from the cell culture vessel, and (B) is a photomicrograph showing the cells on day 8 of culture after they were collected from the cell culture vessel.

In FIG. 7, (A) is a photomicrograph showing the bone marrow-derived mesenchymal stem cells on day 6 of culture before they were collected from the cell culture vessel, and (B) is a photomicrograph on day 6 of culture after the cells were collected from the cell culture vessel.

In FIG. 9, (A) is a photomicrograph showing the synovial-derived mesenchymal stem cells on day 7 of culture before they were collected from the cell culture vessel, and (B) is a photomicrograph on day 7 of culture after the cells were collected from the cell culture vessel.

FIG. 10 includes photographs which shows that cells which have been mass cultured with the cell culture device of the present invention are multipotential cells; wherein (A) is a photograph showing differentiation into chondrocytes, (B) is a photograph showing differentiation into adipocytes, and (C) is a photograph showing differentiation into osteocytes.

DETAILED DESCRIPTION OF VARIOUS EMBODIMENTS

Embodiments of the present invention will be described in detail below while referring to the attached drawings. The embodiments are only intended to facilitate the understanding of the principles of the present invention and the scope of the present invention is not limited to the following embodiments. Other embodiments where a person skilled in the art can appropriately replace configurations of the embodiments below are included within the scope of the present invention.

Figure 1:
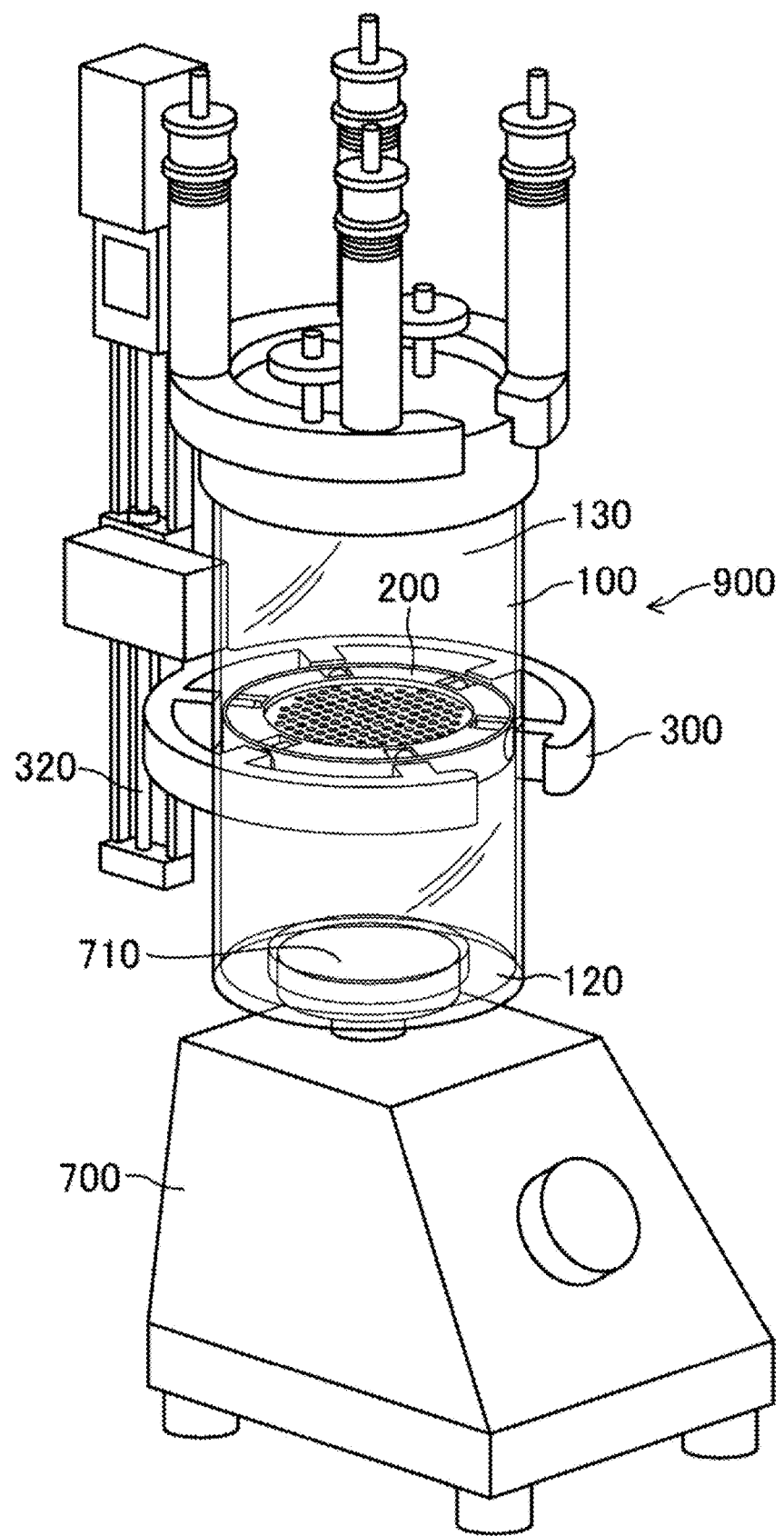
FIG. 1 is a diagram that illustrates the external appearance of a cell culture device according to the present embodiment.

As shown in FIG. 1, the cell culture device 900 according to the present embodiment includes: a cell culture vessel 100, which is approximately a cylindrical body; a dish-shaped body 200, which is approximately a disc-shaped body; and an annular body 300, which is approximately a ring-shaped body. The "approximately a cylindrical body" means a columnar body with a horizontal cross-section that not only may be a circle but also may be an ellipse or an oval. The "approximately a disc-shaped body" means a shape that not only may be a circle but also may be an ellipse or an oval in plan view. The "approximately a ring-shaped body" means a shape that not only may be a circular annular body but also may be an elliptical annular body or an oval-shaped annular body in plan view.

The cell culture vessel 100 includes: an opening, not shown, at its upper end; and a flat bottom part 120 at its lower end. The cell culture vessel 100 includes a hollow space 130 filled with a scaffold that allows for cells to be cultured. The scaffold, a medium, and cells to be cultured can be inserted from the opening at the upper end of the cell culture vessel 100.

The cells to be cultured are not limited to any particular cells and may be cells that are susceptible or are not susceptible to cell damage; however, cells susceptible to cell damage are preferred; examples such as human embryonic stem (ES) cells, iPS cells, and somatic stem cells are more preferred. As somatic stem cells, for example, adipose-derived or bone marrow-derived mesenchymal stem cells are preferred. The medium to be used is a liquid medium and includes, for example, glucose.

There are no particular limitations to the dimensions of the cell culture vessel 100, and the volume may be, for example, 250 ml (diameter: 100 mm, height: 50 mm, bottom: 100 mm), 500 ml (diameter: 100 mm, height: 100 mm, bottom: 100 mm), or 1000 ml (diameter: 100 mm, height: 200 mm, bottom: 100 mm).

The cell culture vessel 100 is a container in which it is difficult for cells to adhere to the inner walls of the vessel. The vessel is made of either a plastic that has low adhesiveness, such as, polyethylene terephthalate, polypropylene, polyethylene, polycarbonate, and polystyrene; or a plastic or glass that has been subjected to a hydrophobic surface treatment, for example, a fluorine treatment or a silicon treatment.

The cells cultured in the cell culture vessel 100 is subjected to vibration in the vertical direction by a vibration part 710 of a vibration device 700. There are no particular limitations to the vibration device 700; however, it may be, for example, a vortex.

The scaffold that fills the space 130 of the cell culture vessel 100 may be, for example, a three-dimensional porous scaffold. The three-dimensional porous scaffold may have, for example, an average porosity of from 50% to 90%, preferably from 80% to 90%, and an average pore size from 10 μm to 800 μm, preferably from 200 μm to 400 μm. The scaffold may either be a single scaffold or an aggregate of a plurality of small pieces that support the cells. There are no particular limitations to the cultivation area of the scaffold and it may be, for example, from 800 cm2 to 900,000 cm2; preferably, from 800 cm2 to 45,000 cm2. In the case where the scaffold is made of an aggregate of a plurality of small pieces that support the cells, it may be, for example, an aggregate of fibers (nonwoven fabric, woven fabric, or knitted fabric) made of thermoplastic resin, or may be an aggregate of sheets made of a thermoplastic resin kneaded before it is formed into the scaffold.

Figure 2:
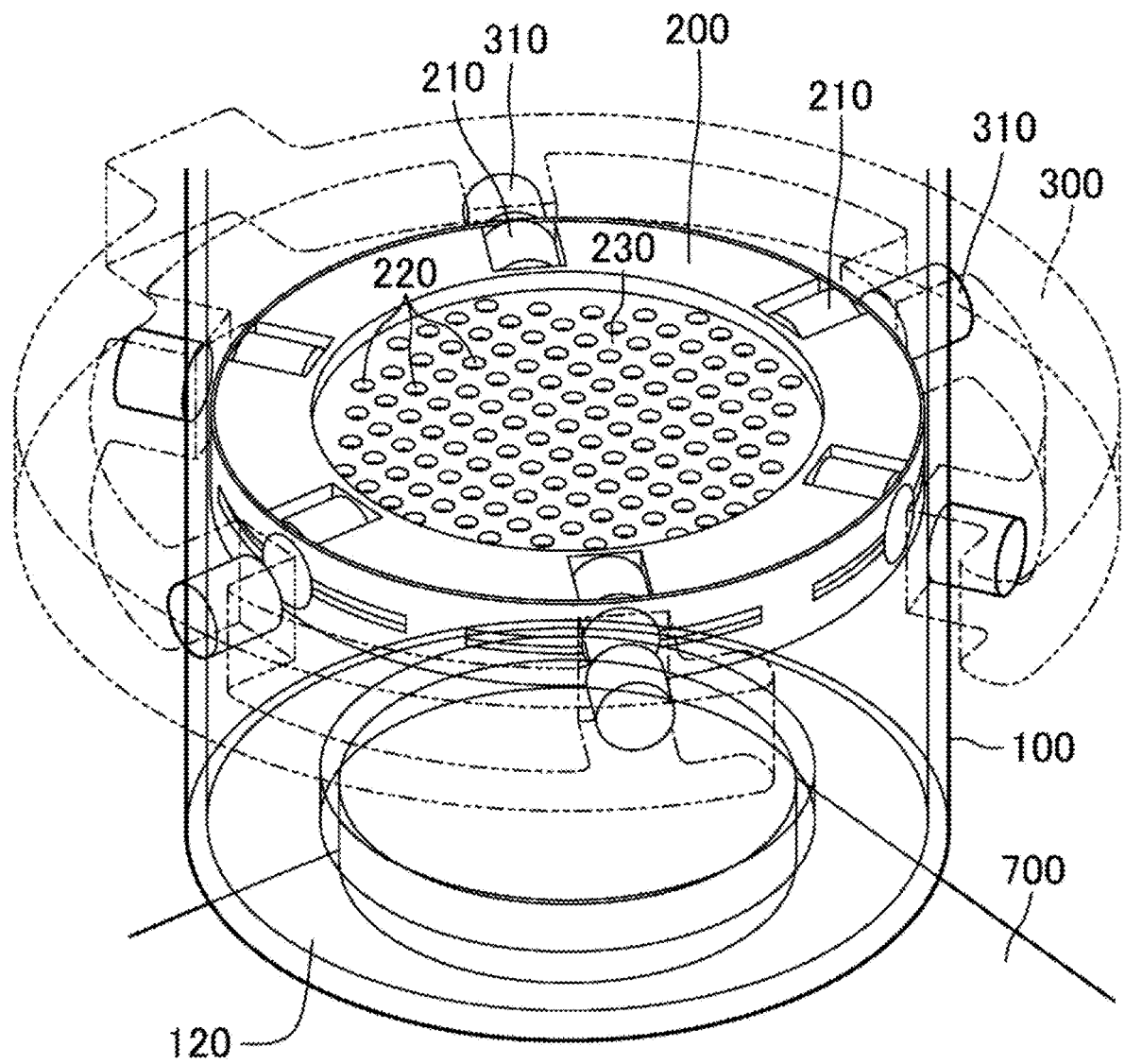
FIG. 2 is a diagram that illustrates in detail the vicinity of a dish-shaped body of the cell culture device according to the present embodiment.

As shown in FIG. 2, the dish-shaped body 200 includes a plurality of magnetic attraction members 210 at a circumferential portion thereof at equal intervals. The dish-shaped body 200 may have, for example, a thickness of 15 mm, an outer diameter of 95 mm, and an inner diameter of 68 mm. The magnetic attraction members 210 are each made of a magnet or a ferromagnetic body. The magnet is a permanent magnet or an electromagnet, and the ferromagnetic body is a metal containing, for example, iron, cobalt or nickel as a main component. There are no particular limitations on the shape of the magnetic attraction member 210, and it may be, for example, a cylindrical body having a diameter of 10 mm and a height of 10 mm. In the present embodiment, six magnetic attraction members 210 are provided at equal intervals of 60 degrees at the circumferential portion of the dish-shaped body 200 that is approximately a disc-shaped body. The magnetic force of the magnetic attraction member 210 may be, for example, from 4500 gausses to 4800 gausses in the case of a permanent magnet, and may be 0 gauss in the case of an iron. The dish-shaped body 200 is horizontally arranged in the hollow space of the cell culture vessel 100. The dish-shaped body 200 that is approximately a disc-shaped body has a diameter that is slightly smaller than the diameter of the cell culture vessel 100 that is approximately a cylindrical body. Specifically, assuming that the inner diameter of the cell culture vessel 100 that is approximately a cylindrical body is D1, the diameter D2 of the dish-shaped body 200 that is approximately a disc-shaped body may be from 0.90D1 to 0.998D1. Thus, the dish-shaped body 200 that is approximately a disc-shaped body does not come into contact with the inner surface of the cell culture vessel 100. Wheels arranged at equal intervals may be provided at a circumferential portion of the dish-shaped body 200 that is approximately a disc-shaped body, so that these wheels and the inner surface of the cell culture vessel 100 may be brought into contact with each other.

The annular body 300 that is approximately a ring-shaped body is positioned outside the cell culture vessel 100 so that the cell culture vessel 100 can be positioned inside the ring. The thickness of the annular body 300 is, for example, 15 mm which is the same as the thickness of the dish-shaped body 200. The annular body 300 that is approximately a ring-shaped body includes a plurality of magnetic attraction members 310 made of magnets, each of which corresponds to associated one of the magnetic attraction members 210 of the dish-shaped body 200. There are no particular limitations on the shape of the magnetic attraction member 310. Similarly to the magnetic attraction members 210, the magnetic attraction member 310 may be, for example, a cylindrical body having a diameter of 10 mm and a height of 10 mm. The magnetic force of magnetic attraction member 310 may be, for example, from 4500 gausses to 4800 gausses in the case of permanent magnets. Each magnetic attraction member 210 of the dish-shaped body 200 may be a magnet, and each magnet may be arranged in the dish-shaped body 200 so that one pole of the magnet is directed to the outside of the vessel; and each magnetic attraction member 310, which is a magnet, of the annular body 300 may be arranged in the annular body 300 so that the other pole of the magnet is directed to the inside of the vessel so as to correspond to associated one of the magnets of the dish-shaped body 200. For example, in a case in which the dish-shaped body 200 includes six permanent magnets each having the S pole directed to the outside of the vessel, the annular body 300 includes six permanent magnets having the N pole directed to the inside of the vessel so as to correspond to associated one of the six permanent magnets of the dish-shaped body 200. Also, for example, in a case in which the magnetic attraction member 210 is made of iron and does not have any polarity, either the N pole or the S pole of each permanent magnet 310 may be directed to the inside of the vessel. The distance between an end portion of one side (for example, the S pole of the magnet) of the magnetic attraction member 210 of the dish-shaped body 200 and an end portion of the other side (for example, the N pole of the magnet) of the magnetic attraction member 310 of the annular body 300 may be, for example, from 0.1 mm to 10.0 mm. Since each magnetic attraction member 310 of the annular body 300 corresponds to associated one of the magnetic attraction members 210 of the dish-shaped body 200, the height of the annular body 300 (i.e., the position of the vertical direction) and the height of the dish-shaped body 200 are the same.

A plurality of through-holes 220 are formed in a central portion of the dish-shaped body 200. There are no particular limitations to the diameter of the through-holes 220 and they may be, for example, from 1 mm to 5 mm.

The annular body 300 is supported by a lifting device 320 and is moved vertically. The annular body 300 is moved vertically, and the dish-shaped body 200 also moves vertically since the dish-shaped body 200 moves in conjunction with the annular body 300 due to a magnetic force. This movement allows agitation of the medium, and oxygenation of the cells and nutrient supply to the cells. The vertical movement of the annular body 300 may be, for example, a single-vibration movement or approximately a single-vibration movement. The cycle of the vertical movement of the annular body 300 may be, for example, from 0.5 times/hour to 12.0 times/hour. The "approximately a single-vibration movement" means, for example, repeating the following movements: moving from downward to upward and stopping for a fixed period of time; then, moving from upward to downward and stopping for a fixed period time; and then moving again from downward to upward. The stroke length of the vertical movement of the annular body 300 is shorter than the height of the cell culture vessel 100, and may be set to, for example, from 20 mm to 120 mm. The speed of the upward or downward movement of the annular body 300 may be, for example, from 0.5 mm/sec to 10.0 mm/sec.

Figure 3:
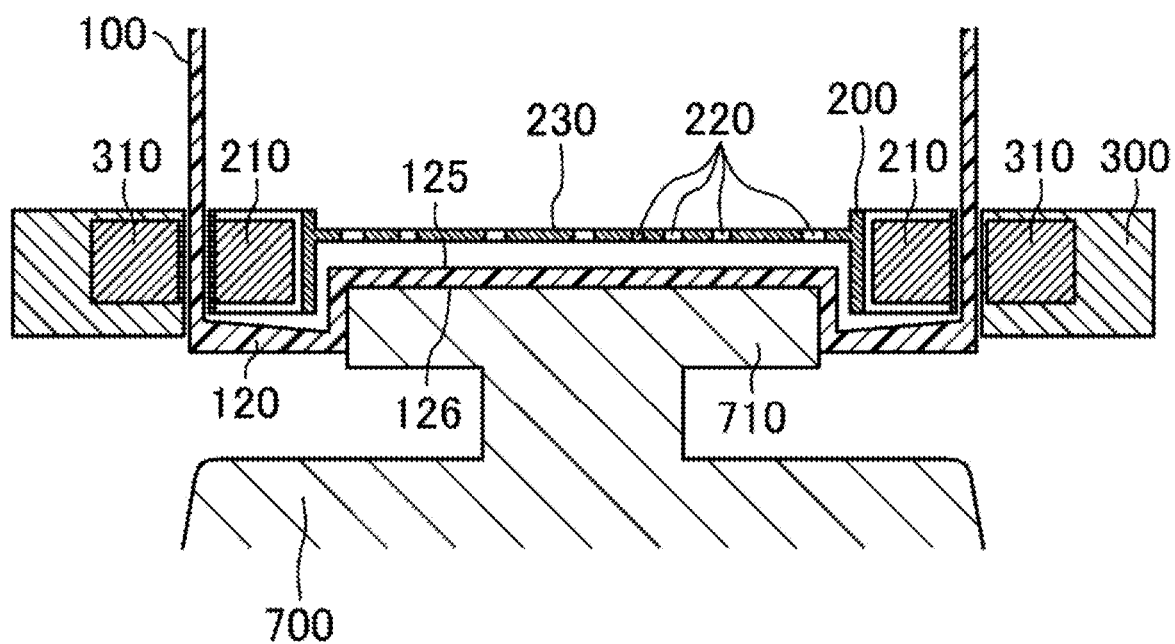
FIG. 3 is a diagram that illustrates in detail the vicinity of the bottom part of a cell culture vessel of the cell culture device according to the present embodiment.

As shown in FIG. 3, the cell culture vessel 100 includes a bottom projected portion 125 at a central portion of the bottom part 120. The bottom projected portion 125 protrudes upward and has a hollow space inside. In other words, the cell culture vessel 100 has a bottom recess 126 having a shape corresponding to the bottom projected portion 125 at the central portion of the bottom part 120. For example, in a case in which the diameter of the bottom part 120 of the cell culture vessel 100 is 100 mm, the depth of the bottom recess 126 is 8 mm and the diameter of the inside of the bottom recess 126 is 60 mm. The vibration part 710 of the vibration device 700 is fitted into the bottom recess 126 without any gaps.

The dish-shaped body 200 includes, in a central portion of its bottom surface, a dish recess 230 into which the bottom projected portion 125 of the cell culture vessel 100 is fitted. Although a gap between the bottom projected portion 125 of the cell culture vessel 100 and the dish recess 230 of the dish-shaped body 200 is illustrated in FIG. 3, the bottom projected portion 125 may be fitted into the dish recess 230 without any gaps.

Next, how to use the cell culture device according to the present embodiment will be described.

First, the dish-shaped body 200 arranged in the hollow space 130 of the cell culture vessel 100 is positioned in the vicinity of a lower part of the cell culture vessel 100. In this case, since the height of the annular body 300 and the height of the dish-shaped body 200 are the same, the annular body 300 is also positioned in the vicinity of the lower part of the cell culture vessel 100. Then, the scaffold, the medium, and the cells to be cultured are placed in the space 130 of the cell culture vessel 100 from the opening (not shown) at the upper end of the cell culture vessel 100.

Next, the annular body 300 positioned in the vicinity of the lower part of the cell culture vessel 100 is moved upward. Each of the magnetic attraction members 310 of the annular body 300 corresponds to associated one of the magnetic attraction members 210 of the dish-shaped body 200, and the annular body 300 and the dish-shaped body 200 move in conjunction with each other due to a magnetic force. Thus, the dish-shaped body 200 is also moved upward. When the dish-shaped body 200 is moved upward, the scaffold filling the hollow space 130 of the cell culture vessel 100 and the cells adhered to the scaffold are pushed up from below by the dish-shaped body 200 and moved upward. Although the dish-shaped body 200 moves upward, the medium in the space 130 of the cell culture vessel 100 is not pushed upward but passes through the plurality of through-holes 220 formed in the central portion of the dish-shaped body 200. This movement causes the medium to be agitated.

Next, the movement of the annular body 300 is stopped when the dish-shaped body 200 is positioned in the vicinity of an upper portion of the cell culture vessel 100. Assuming that the height of the cell culture vessel 100 is L (the height L is a distance from the opening at the upper end of the cell culture vessel 100 to the bottom part 120), positioning the dish-shaped body 200 in the vicinity of the upper portion of the cell culture vessel 100 means that the dish-shaped body 200 is positioned below the upper end of the cell culture vessel 100 by a distance of, for example, from 0.3 L to 0.7 L. In the state in which the dish-shaped body 200 is positioned in the vicinity of the upper portion of the cell culture vessel 100, the medium is not pushed upward, and the cells, for example, can undergo oxygenation.

Next, the annular body 300 is moved downward. The annular body 300 and the dish-shaped body 200 move in conjunction with each other due to the magnetic force, which means that the dish-shaped body 200 is also moved downward. When the dish-shaped body 200 moves downward, the scaffold and the cells adhered to the scaffold fall with gravity, and the cells become immersed in the medium and are supplied with nutrients.

The movement of the annular body 300 is stopped when the dish-shaped body 200 is positioned in the vicinity of a lower portion of the cell culture vessel 100. Positioning the dish-shaped body 200 in the vicinity of the lower portion of the cell culture vessel 100 includes positions from where the dish recess 230 of the dish-shaped body 200 is fitted to the bottom projected portion 125 of the cell culture vessel 100 without any gaps to where the dish-shaped body 200 is positioned above the bottom part 120 of the cell culture vessel 100 by a distance of, for example, from 0.01 L to 0.2 L.

After that, the annular body 300 is moved upward again. The annular body 300 and the dish-shaped body 200, which moves in conjunction with the annular body 300 due to the magnetic force, together make vertical movements in this manner.

After the cells are cultured, the dish recess 230 of the dish-shaped body 200 is fitted into the bottom projected portion 125 of the cell culture vessel 100 without any gaps, and the vibration part 710 of the vibration device 700 is fitted into the bottom recess 126 of the cell culture vessel 100 without any gaps. The vibration device 700 is operated in this state so that, for example, vibrations in the vertical direction are transmitted from the vibration part 710 to the cultured cells in the cell culture vessel 100. In this way, cultured cells deeply implanted in the three-dimensional porous scaffold can be easily be collected.

EXAMPLES

Example 1

The dish-shaped body arranged in the hollow space of the cell culture vessel was positioned to be in the vicinity of the lower portion of the cell culture vessel. A scaffold, a medium, and cells to be cultured were placed into the hollow space of the cell culture vessel from the opening at the upper end of the cell culture vessel. The cells used were $5.0 \times 10^7$ adipose-derived mesenchymal stem cells (ADSCs). As the scaffold (3D cell culture), 5,000 sheets of BioNOC II Matrix manufactured by Clean Energy Service Co., Ltd. ("CESCO") were used. The stroke length of the vertical movement of the annular body was set to 60 mm, and the speed of the upward or downward movement of the annular body was set to 1.0 mm/sec. The cycle of the vertical movement of the annular body was set to 1.0 times/hour. The cells were cultured for eight days.

Figure 4:
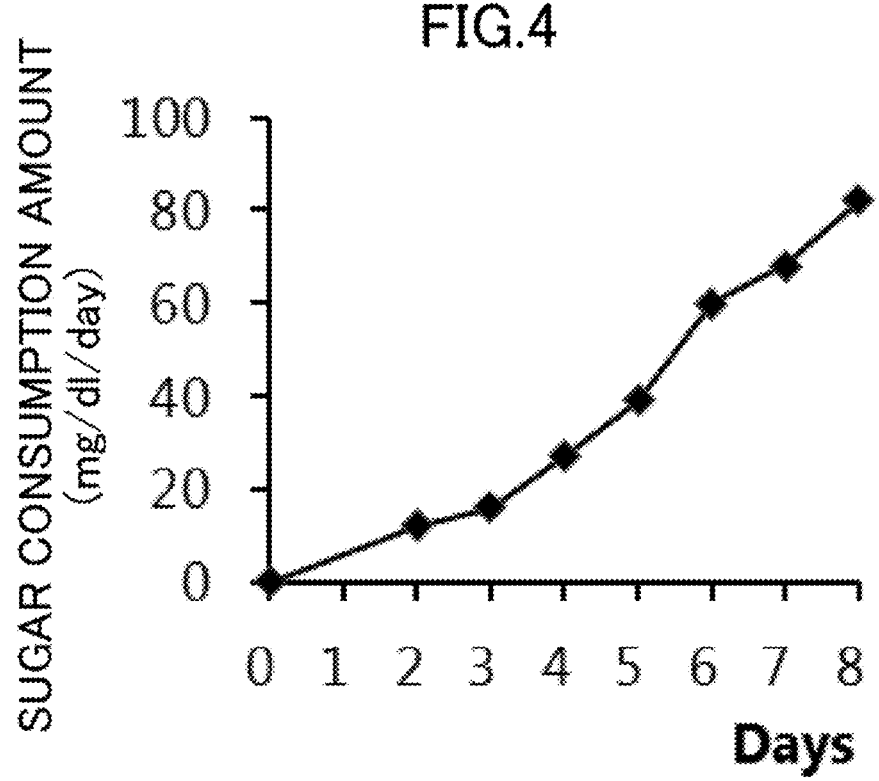
FIG. 4 is a diagram that illustrates the amount of sugar consumption (mg/dL/day) of adipose-derived mesenchymal stem cells for each day culture.

FIG. 4 is a diagram that illustrates the amount of sugar consumption (mg/dL/day) of the cells for each day of culture. The amount of sugar consumption of the cells was measured using a GlucCell Handy Glucose Monitor (manufactured by CESCO). As shown in FIG. 4, it was shown that the cells were appropriately cultured by using the cell culture device according to the present example.

On day 8, a large amount of ADSCs, i.e., $3.2 \times 10^8$ ADSCs, were collected from within the cell culture vessel. While it is difficult to efficiently collect the cultured cells deeply implanted in a three-dimensional porous scaffold without damaging the cultured cells, a large amount of cultured cells can be collected from the cell culture vessel by adding, after cultivation, an enzyme solution including trypsin-EDTA and caseinase into the cell culture vessel so that enzyme treatment can be applied to the cultured cells. FIG. 5(A) is a photomicrograph on day 8 of culture before the cells were collected from the cell culture vessel, and FIG. 5(B) is a photomicrograph on day 8 of culture after the cells were collected from the cell culture vessel. It can be understood from FIG. 5 that a large amount of cultured cells could be properly collected with the cell culture device according to the present example.

As a comparative example, $5.0 \times 10^7$ ADSCs were seeded into a cell culture dish (2D cell culture) manufactured by Sumitomo Bakelite Co., Ltd., and were cultured for 8 days. Table 1 below shows the properties of the cells cultured using the cell culture device (3D cell culture) according to the present example and the properties of the cells cultured using the culture dish (2D cell culture) according to the comparative example. As shown in Table 1, the cells cultured using the cell culture device according to the present example had the same properties as the cells cultured using the conventional cell culture dish.

TABLE 1

| ADSC | Positive Marker | | | | Negative Marker | | |
|---|---|---|---|---|---|---|---|
| | CD13 | CD73 | CD90 | CD105 | CD31 | CD45 | |
| Culture Dish (2D) | 99.98 | 99.89 | 99.98 | 100 | 0.19 | 0.03 | |
| Bottle (3D) | 99.97 | 99.62 | 99.9 | 99.7 | 0.13 | 0.02 | (%) |

Example 2

The cells used in example 1 were ADSCs. In example 2, an attempt to culture bone marrow-derived mesenchymal stem cells (BMSCs) was carried out.

The dish-shaped body arranged in the hollow space of the cell culture vessel was positioned to be in the vicinity of the lower portion of the cell culture vessel. A scaffold, a medium, and cells to be cultured were placed into the hollow space of the cell culture vessel from the opening at the upper end of the cell culture vessel. The cells used were $3.0 \times 10^7$ BMSCs. As the scaffold (3D cell culture), 2,000 sheets of BioNOC II Matrix manufactured by Clean Energy Service Co., Ltd. ("CESCO") were used. The stroke length of the vertical movement of the annular body was set to 40 mm, and the speed of the upward or downward movement of the annular body was set to 1.0 mm/sec. The cycle of the vertical movement of the annular body was set to 1.0 times/hour. The cells were cultured for six days.

Figure 6:
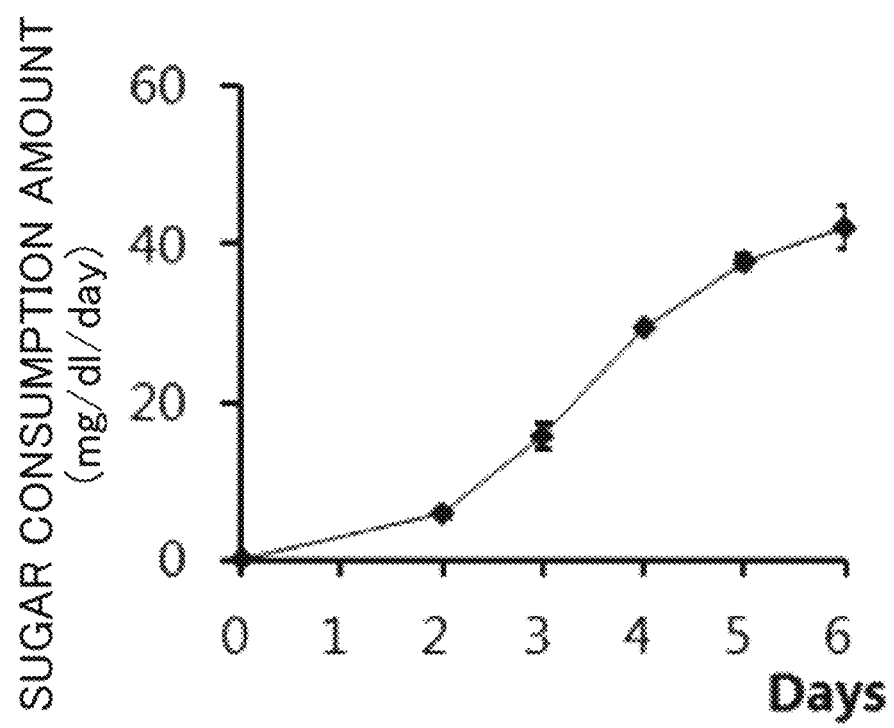
FIG. 6 is a diagram that illustrates the amount of sugar consumption (mg/dL/day) of bone marrow-derived mesenchymal stem cells for each day of culture.

FIG. 6 is a diagram that illustrates the amount of sugar consumption (mg/dL/day) of the cells for each day of culture. The amount of sugar consumption of the cells was measured using a GlucCell Handy Glucose Monitor (manufactured by CESCO). As shown in FIG. 6, it was shown that the cells were appropriately cultured by using the cell culture device according to the present example.

On day 6, a large amount of BMSCs, i.e., $5.42 \times 10^8$ ADSCs, were collected from within the cell culture vessel. A large amount of cultured cells was collected from the cell culture vessel by adding, after cultivation, an enzyme solution including trypsin-EDTA and caseinase into the cell culture vessel so that enzyme treatment can be applied to the cultured cells. FIG. 7(A) is a photomicrograph on day 6 of culture before the cells were collected from the cell culture vessel, and FIG. 7(B) is a photomicrograph on day 6 of culture after the cells were collected from the cell culture vessel. It can be understood from FIG. 7 that a large amount of cultured cells could be properly collected with the cell culture device according to the present example.

As a comparative example, $3.0 \times 10^7$ BMSCs were seeded into a cell culture dish (2D cell culture) manufactured by Sumitomo Bakelite Co., Ltd., and were cultured for 6 days. Table 2 below shows the properties of the cells cultured using the cell culture device (3D cell culture) according to the present example and the properties of the cells cultured using the culture dish (2D cell culture) according to the comparative example. As shown in Table 2, the cells cultured using the cell culture device according to the present example had the same properties as the cells cultured using the conventional cell culture dish.

TABLE 2

| BMSC | Positive Marker | | | | Negative Marker | |
|---|---|---|---|---|---|---|
| | CD13 | CD73 | CD90 | CD105 | CD31 | CD45 |
| Culture Dish (2D) | 99.98 | 99.86 | 96.04 | 99.63 | 0.09 | 0.02 |
| Bottle (3D) | 100 | 99.6 | 97.51 | 99.1 | 0 | 0 (%) |

Example 3

Synovial-derived mesenchymal stem cells are useful for regenerating cartilage and the meniscus because they have a very high cartilage differentiation capacity and proliferation ability. In example 3, an attempt to culture synovial-derived mesenchymal stem cells was carried out.

The dish-shaped body arranged in the hollow space of the cell culture vessel was positioned to be in the vicinity of the lower portion of the cell culture vessel. A scaffold, a medium, and cells to be cultured were placed into the hollow space of the cell culture vessel from the opening at the upper end of the cell culture vessel. The cells used were $1.5 \times 10^7$ synovial-derived mesenchymal stem cells. As the scaffold (3D cell culture), 3,000 sheets of BioNOC II Matrix manufactured by Clean Energy Service Co., Ltd. ("CESCO") were used. The stroke length of the vertical movement of the annular body was set to 45 mm, and the speed of the upward or downward movement of the annular body was set to 1.0 mm/sec. The cycle of the vertical movement of the annular body was set to 1.0 times/hour. The cells were cultured for seven days.

Figure 8:
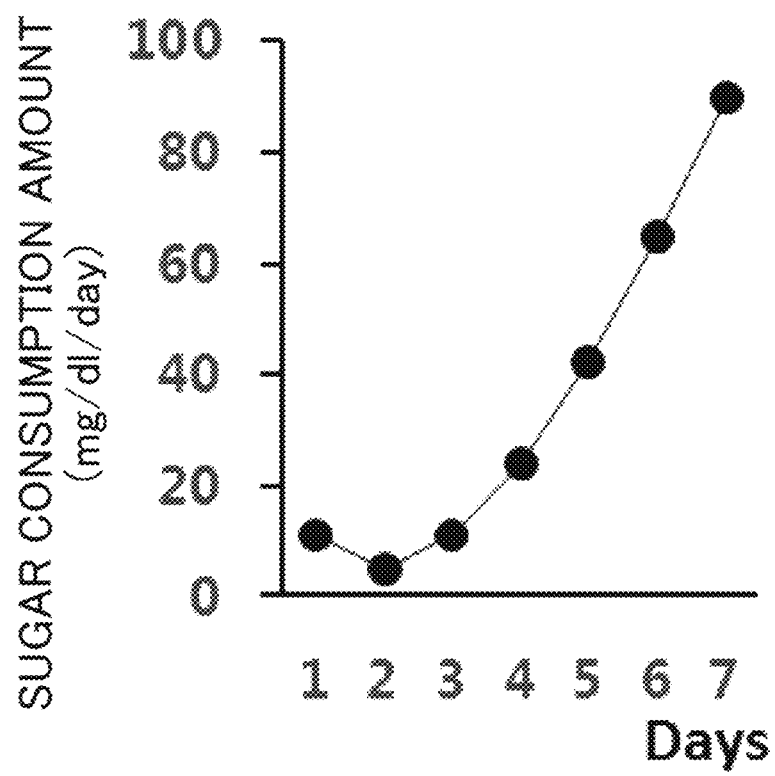
FIG. 8 is a diagram that illustrates the amount of sugar consumption (mg/dL/day) of synovial-derived mesenchymal stem cells for each day of culture.
Figure 11:
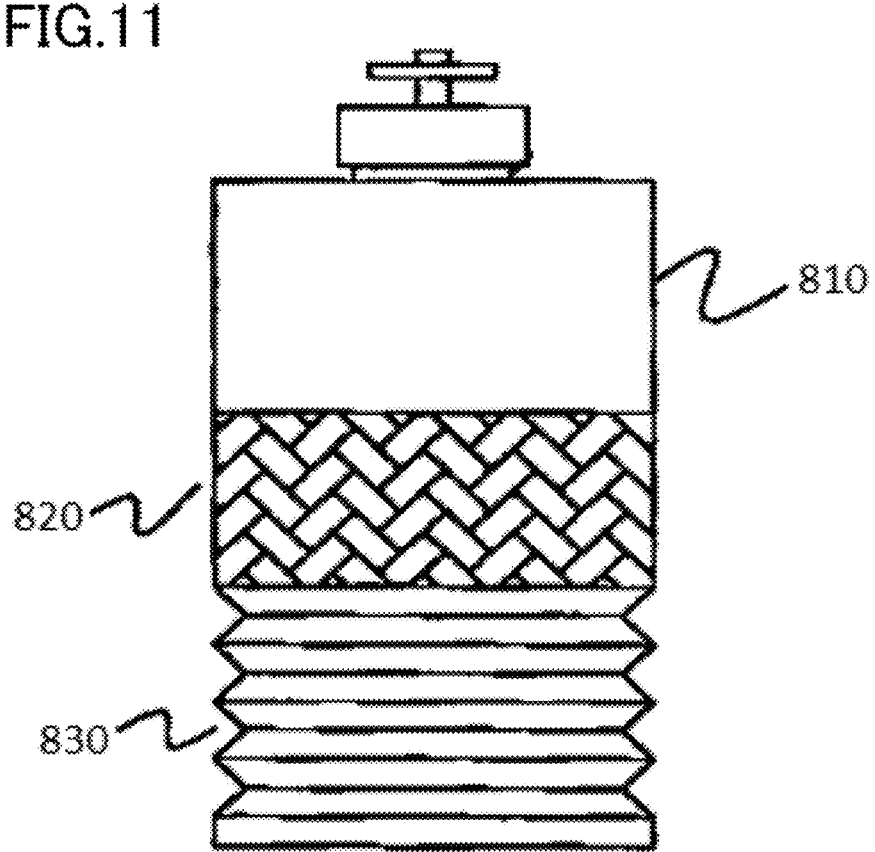
FIG. 11 is a diagram that illustrates a conventional cell culture device with a bellows-shaped chamber in an uncompressed shape.
Figure 12:
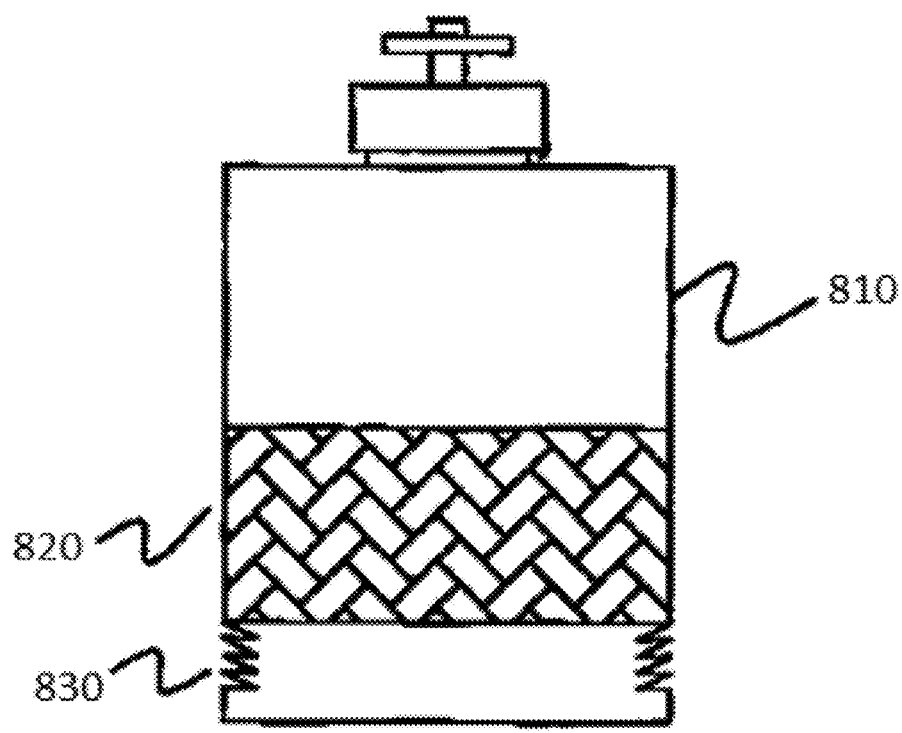
FIG. 12 is a diagram that illustrates a conventional cell culture device with a bellows-shaped chamber in a compressed shape.

FIG. 8 is a diagram that illustrates the amount of sugar consumption (mg/dL/day) of the cells for each day of culture. The amount of sugar consumption of the cells was measured using a GlucCell Handy Glucose Monitor (manufactured by CESCO). As shown in FIG. 8, it was shown that the cells were appropriately cultured by using the cell culture device according to the present example.

On day 7, a large amount of synovial-derived mesenchymal stem cells, i.e., $1.2 \times 10^8$ synovial-derived mesenchymal stem cells, were collected from within the cell culture vessel. A large amount of cultured cells was collected from the cell culture vessel by adding, after cultivation, an enzyme solution including trypsin-EDTA, caseinase, and collagenase into the cell culture vessel so that enzyme treatment can be applied to the cultured cells. The enzyme solution included 1 mg/ml of trypsin-EDTA, 3.334 mg/ml of caseinase, and 1 mg/ml of collagenase. FIG. 9(A) is a photomicrograph on day 7 of culture before the cells were collected from the cell culture vessel, and FIG. 9(B) is a photomicrograph on day 7 of culture after the cells were collected from the cell culture vessel. It can be understood from FIG. 9 that a large amount of cultured cells could be properly collected with the cell culture device according to the present example.

Example 4

To check the preservation of stem cell properties and pluripotency of the synovial-derived mesenchymal stem cells after the mass cultivation, induced differentiation of the synovial-derived mesenchymal stem cells that had been mass cultured and collected according to example 3 to adipocytes, chondrocytes, and osteocytes was carried out. A Human Mesenchymal Stem Cell Functional Identification Kit manufactured by R&D System Inc. was used for the induced differentiation. After $10^4$ cells were adhered to each of 24-well cell culture plates, the cells were cultured for 14 days for induced differentiation to adipocytes, using a differentiation medium obtained by adding Adipogenic Supplement and ITS Supplement, which were included with the kit, to 50 ml of DMEM basal medium. For induced differentiation to chondrocytes, the cells were cultured for 21 days using a differentiation medium obtained by adding Chondogenic Supplement and ITS Supplement, which were included with the kit, to 50 ml of DMEM basal medium. For induced differentiation of osteocytes, the cells were cultured for 21 days using a differentiation medium obtained by adding Osteogenic Supplement and ITS Supplement, which were included with the kit, to 50 ml of DMEM basal medium. To identify the adipocytes, chondrocytes, and osteocytes after the induced differentiation, the cells were stained with OilRed-O, Alcia Blue, and Alizaric Red after 4% paraformaldehyde fixation. FIG. 10 includes photographs which shows that cells which have been mass cultured with the cell culture device of the present invention are multipotential cells; wherein (A) is a photograph showing differentiation into chondrocytes, (B) is a photograph showing differentiation into adipocytes, and (C) is a photograph showing differentiation into osteocytes. The photograph (A) shows the cells stained with Alcian Blue. The photograph (B) shows the cells stained with Oil Red 0. The photograph (C) shows the cells stained with Alizarin Red. As shown in FIG. 10, the synovial-derived mesenchymal stem cells after being mass cultured retained stem cell properties and pluripotency, and were differentiated into adipocytes, chondrocytes, and osteocytes.

The cell culture device can be used for culturing cells.

DESCRIPTION OF REFERENCE CHARACTERS

110 Cell Culture Vessel
120 Bottom Part
125 Bottom Projected Portion
126 Bottom Recess
130 Space
200 Dish-shaped Body
220 Through-hole
230 Dish Recess
210 Magnetic Attraction Member
300 Annular Body
310 Magnetic Attraction Member
320 Lifting Device
700 Vibration Device
710 Vibration Part
900 Cell Culture Device

The invention claimed is:

1. A cell culture device, comprising:
a cell culture vessel which is approximately a cylindrical body having a flat bottom part at a lower end and a hollow space to be filled with a scaffold for culturing cells;
one dish-shaped body which is approximately disc-shaped, includes a central portion in which a plurality of through-holes are formed as columnar spaces, and which has a diameter slightly smaller than a diameter of the approximately cylindrical body as the cell culture vessel, the dish-shaped body including a plurality of magnetic attraction members made of magnets or ferromagnets arranged at equal intervals at a circumferential portion of the dish-shaped body, the dish-shaped body being arranged horizontally in the hollow space of the cell culture vessel so as not to come into contact with an inner wall of the cell culture vessel; and
an annular body which is approximately ring shaped and configured to move in a vertical direction, the annular body including a plurality of magnetic attraction members made of magnets each corresponding to, and attracting with a magnetic force, associated one of the magnetic attraction members of the dish-shaped body, the annular body being arranged on an outer side of the cell culture vessel so as to position the cell culture vessel within the annular body, the annular body moving upward and causing the dish-shaped body to move upward in conjunction with the upward movement of the annular body due to the magnetic force so that the scaffold filling the hollow space of the cell culture vessel is pushed up from a bottom, and the annular body moving downward and causing the dish-shaped body to move downward in conjunction with the downward movement of the annular body due to the magnetic force so that the scaffold filling the hollow space of the cell culture vessel falls with gravity.

2. The cell culture device of claim 1, wherein:
the magnetic attraction members of the dish-shaped body are magnets, and each of the magnets is arranged in the dish-shaped body with one pole directed to the outside of the vessel; and each of the magnets of the annular body is arranged in the annular body with the other pole directed to the inside of the vessel such that each of the magnets of the annular body corresponds to associated one of the magnets of the dish-shaped body.

3. The cell culture device of claim 1, wherein:
the cell culture vessel includes a bottom projected portion at a central portion of the bottom part, the bottom projected portion protruding upward and having a hollow space inside, and also includes at the central portion of the bottom part, a bottom recess which has a shape corresponding to the bottom projected portion and into which a vibration part of a vibration device for applying vibration in the vertical direction to the cells cultured is fitted; and
the dish-shaped body includes, at a central portion of a lower surface of the dish-shaped body, a dish recess to which the bottom projected portion of the cell culture vessel is fitted.

4. The cell culture device of claim 2, wherein:
the cell culture vessel includes a bottom projected portion at a central portion of the bottom part, the bottom projected portion protruding upward and having a hollow space inside, and also includes at the central portion of the bottom part, a bottom recess which has a shape corresponding to the bottom projected portion and into which a vibration part of a vibration device for applying vibration in the vertical direction to the cells cultured is fitted; and
the dish-shaped body includes, at a central portion of a lower surface of the dish-shaped body, a dish recess to which the bottom projected portion of the cell culture vessel is fitted.

5. The cell culture device of claim 1, further comprising a scaffold in the hollow space, wherein the scaffold is an aggregate of a plurality of small pieces that support the cells.

6. The cell culture device of claim 2, further comprising a scaffold in the hollow space, wherein the scaffold is an aggregate of a plurality of small pieces that support the cells.

7. The cell culture device of claim 3, further comprising a scaffold in the hollow space, wherein the scaffold is an aggregate of a plurality of small pieces that support the cells.

8. The cell culture device of claim 1, wherein the cells to be cultured are mesenchymal stem cells.

9. The cell culture device of claim 2, wherein the cells to be cultured are mesenchymal stem cells.

10. The cell culture device of claim 3, wherein the cells to be cultured are mesenchymal stem cells.

11. The cell culture device of claim 5, wherein the cells to be cultured are mesenchymal stem cells.

* * * * *